United States Patent [19]

Strimling

[11] Patent Number: 5,133,743
[45] Date of Patent: Jul. 28, 1992

[54] ARTIFICIAL HEART WITH PUMP CONTROL SYSTEM

[76] Inventor: Walter E. Strimling, Weston, Mass.

[21] Appl. No.: 560,117

[22] Filed: Jul. 31, 1990

[51] Int. Cl.$^5$ .............................................. A61F 2/22
[52] U.S. Cl. .......................................................... 623/3
[58] Field of Search ............................. 623/3; 417/394

[56] References Cited

U.S. PATENT DOCUMENTS 4,231,354  11/1980  Kurtz et al. ............................. 623/3

Primary Examiner—David Isabella
Attorney, Agent, or Firm—Herbert M. Shapiro

[57] ABSTRACT

A pump and valve system having particular use as an artifical heart for human or animal implantation has long-lasting wear characteristics by imparting a relatively slow start ramp to the drive voltage for the pump drive. The ramp reduces the shock to the valves and thus reduces wear. The relatively slow ramp-down of the drive voltage also reduces wear similarly.

3 Claims, 4 Drawing Sheets

VARIABLE SPEED PUMP CONTROL CIRCUIT

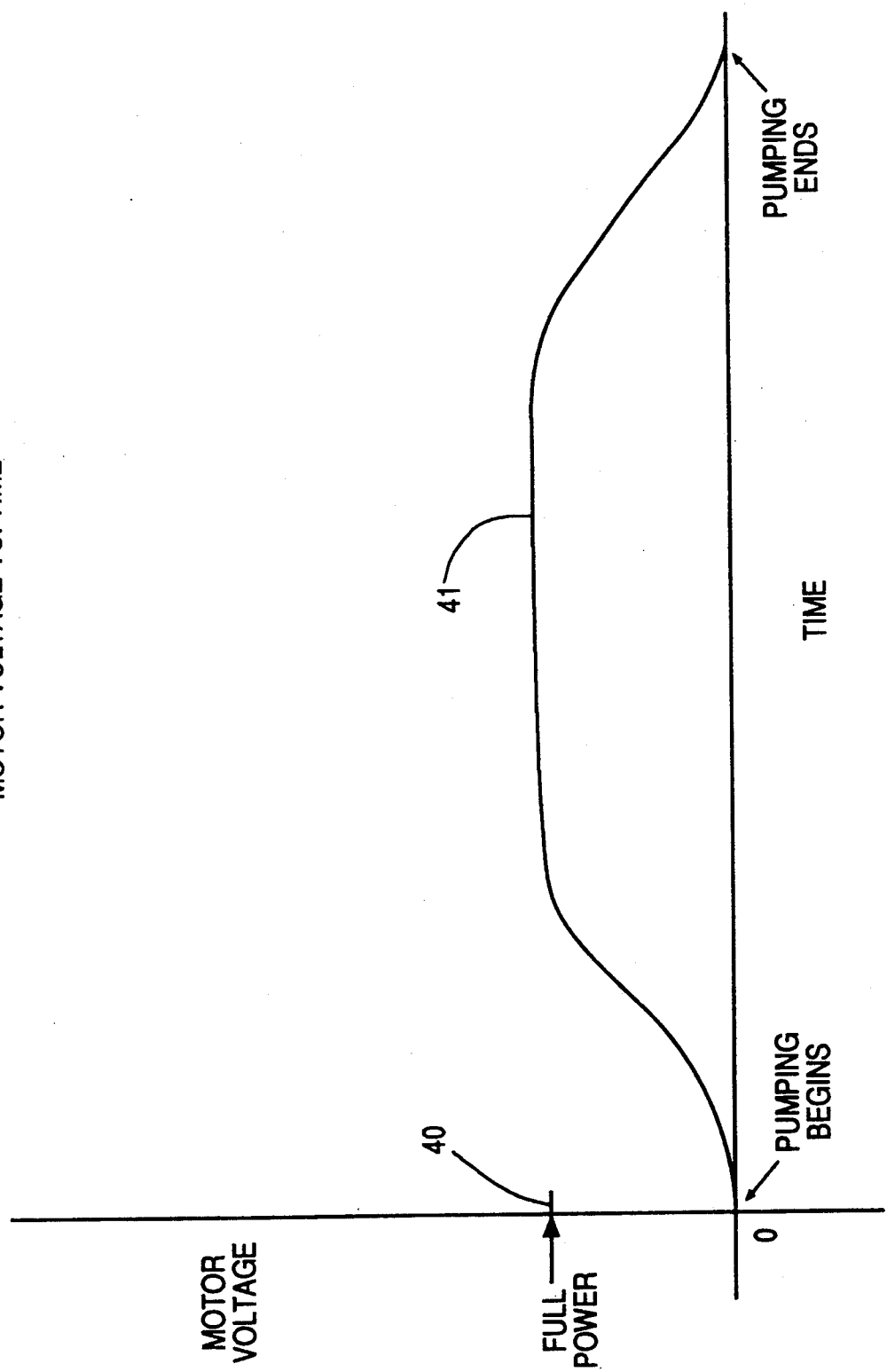

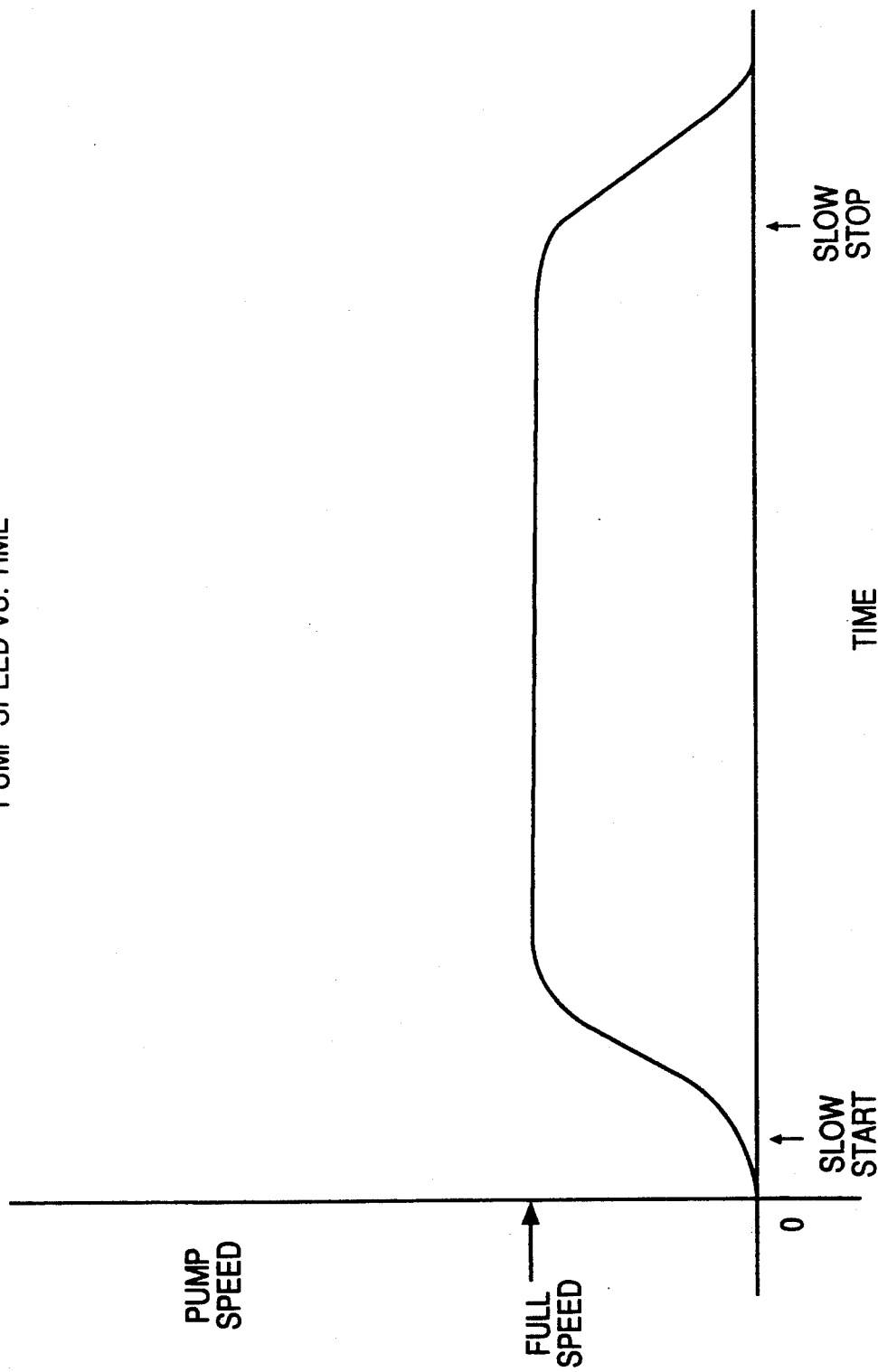

ARTIFICIAL HEART WITH PUMP CONTROL SYSTEM

FIELD OF THE INVENTION

This invention relates to pump control systems and more particularly to artificial hearts for replacement of defective human or animal hearts.

BACKGROUND OF THE INVENTION

When a person loses the full efficiency of one of the valves in his or her living heart, an operation is sometimes performed to implant an artificial valve. The artificial valves that are substituted for the original living tissue valves are sometimes made of animal membranes and sometimes made of metal or plastic or both. The purpose of these valves is to allow flow in only one direction, preventing back flow. These valves are usually called "check valves".

The original heart valves made of living tissue normally repair themselves, so wear is not a common problem. But, living tissue heart valves fail for other reasons. In some cases, a living tissue valve may fail to close completely when the flow pressure reverses, due to disease and/or birth defect. In any case, replacement valves are frequently required. The artificial valve that is implanted has no repair mechanism so it wears out. Eventually, it has to be replaced with a new artificial valve.

When the heart itself is replaced with a mechanical device, that is an artificial heart, the heart valves are also replaced with artificial valves. So there are two types of critical mechanisms that will wear with no living repair mechanism: the artificial heart and the mechanical check valves.

Doctors using mechanical replacement valves in animal tests of artificial hearts are finding that the mechanical valves often wear out much faster than the same mechanical valves implanted in a human heart.

The present logic in the performance of available artificial hearts is to make the heart beat at the same rate as the living heart that it replaces and to deliver the same volume as the living heart would deliver. Relatively little attention is paid to the shape of the pressure vs time graph characterizing the operation of the artificial heart, except to have the total time of pressurization approximately the same as for a living heart and except that careful attention is paid to be sure that the pressure gradient for the mechanical heart does not get so high as to injure blood cells.

Because available mechanical hearts are merely turned on and off abruptly or are possible programmed simply to avoid high pressure which would damage blood cells, they operate to transmit more shock to the mechanical valves than the living heart does, thus producing early failure of the mechanical valves.

BRIEF DESCRIPTION OF AN ILLUSTRATIVE EMBODIMENT OF THIS INVENTION

The present invention is based on the realization that rapid wear of mechanical replacement valves for the replacement mechanical heart is due to the fact that the pump for the heart is not controlled in a manner to regulate blood pressure to follow the natural (relatively slow) changes in blood pressure which occur during each pump cycle. In accordance with such a realization, an artificial heart replacement for a human or animal heart includes a control circuit for the heart pump drive device which is operative to start the pump slowly and to gradually increase pressure during each cycle of operation. The control circuit also is operative to stop the pump slowly during each cycle rather than abruptly as is now the case in present artificial heart systems.

BRIEF DESCRIPTION OF THE DRAWING

FIGS. 3 and 4 are graphs of motor voltage and pump speed versus time respectively.

DETAILED DESCRIPTION OF AN ILLUSTRATIVE EMBODIMENT OF THIS INVENTION

Figure 1:
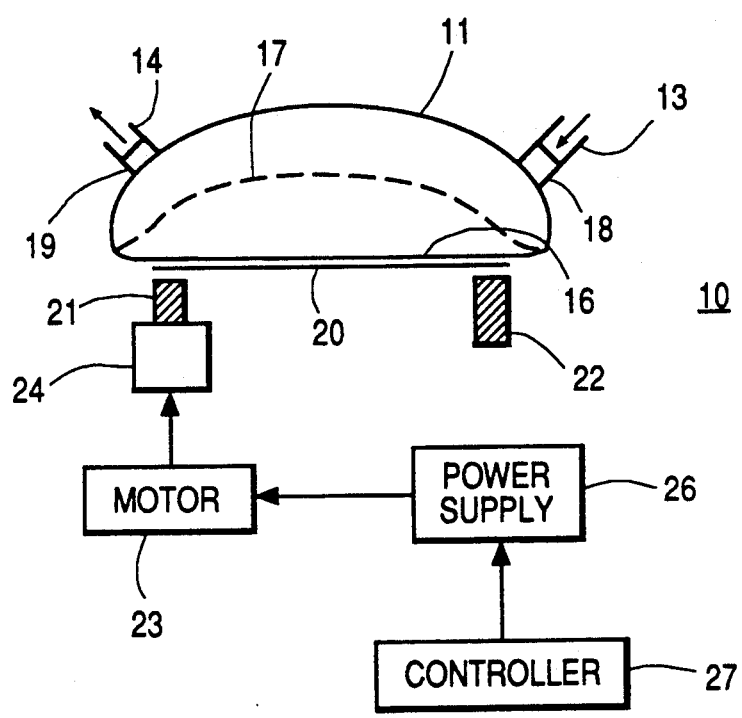
FIG. 1 is a schematic diagram of a prior art artificial heart.

FIG. 1 shows a representative artificial heart 10. The heart comprises a central chamber 11 with blood inlet and outlets 13 and 14. The bottom portion of the chamber moves periodically along a vertical axis between the position shown by solid line 16 and the position shown by broken line 17. This periodic movement of the bottom portion of the heart reduces the volume of the chamber and causes the pumping of blood.

The direction in which blood is pumped is determined by the status of check valves 18 and 19 in the inlet and outlet 13 and 14, respectively. When the bottom of chamber 11 is moving toward the position of line 16, check valve 19 is closed and check valve 18 is open. Thus, blood is flowing into chamber 11 during a "fill" phase. When the bottom of the chamber is moving toward the position of line 17, check valve 19 is opened and check valve 18 closes during an "empty" phase. The check valves are configured to operate in this reciprocal manner conveniently by the incipient changes in pressure in the chamber due to the changing position of the chamber bottom.

The drive mechanism for moving the chamber bottom includes a pusher plate 20 which communicates with a ramp-shaped circular cam having a greater vertical dimension to the left, as viewed, than it does to the right as indicated in cross section by blocks 21 and 22 respectively. A motor 23 drives roller member 24 to orbit in a manner to engage the ramp-shaped cam, thus causing periodic vertical displacement of the pusher plate and thus the chamber bottom.

Figure 2:
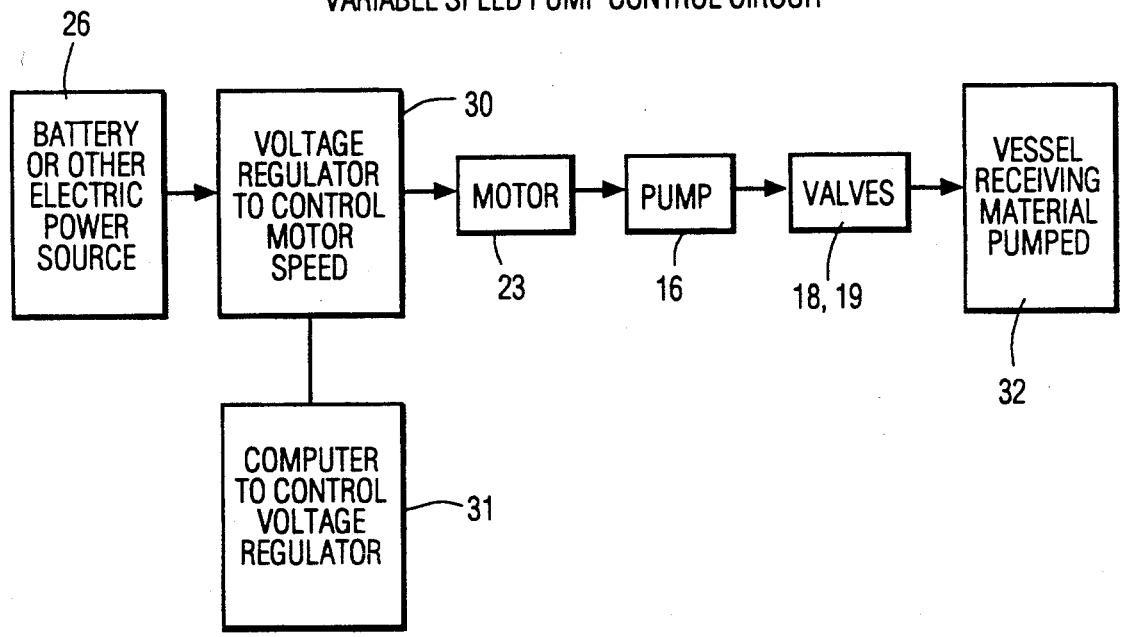
FIG. 2 is a schematic block diagram of a control circuit for the heart of FIG. 1.

The power supply 26 for motor 23 is controlled by controller 27 to regulate the voltage supplied to the motor in accordance with the principles of this invention. FIG. 2 shows a block diagram of a variable speed pump control circuit. Specifically, FIG. 2 shows a battery or other power source supplying power to a voltage regulator 30 for motor 23 of FIG. 2. The figure also shows a computer or microprocessor represented by block 31 for controlling regulator 30. Block 31 is assumed to include a digital to analog converter to convert the digital output of the processor to an analog signal for controlling regulator 30.

Motor 23 drives a pump which, in FIG. 1, comprises the bottom of chamber 11. The movement of the pump operates the check valves 18 and 19. The contents of chamber 11 moves, illustratively, into the arteries of the body as indicated by block 32.

FIG. 3 is a graph showing motor voltage on the y axis and time on the x axis. Full power, typically 12 volts, is indicated at 40. Curve 41 occupies about ½ second of time, assuming a sixty beat per minute normal heart beat, the fill cycle of the heart occupying one half the one-second period. Illustratively, the ramp-up portion of the motor voltage occupies ¼ second, the level portion of the voltage curve occupies ⅝ths second and the ramp-down portion occupies ⅛th second.

FIG. 4 shows a graph of the pump speed plotted against time and can be seen to follow the motor voltage curve of FIG. 3. The ramp-up portion begins asymptotically with respect to the x axis (time) following a portion of an imaginary parabolic curve, symmetrical about the y axis, for the first ⅛th second of a pump phase at which point the slope is 45 degrees, following a 45 degree slope straight line for the next 3/32nds second and following a portion of a circular curve for the final 1/32nd second, where the circular curve is tangent at one end to the 45 degree slope straight line and tangent at the other end to the horizontal line.

The ramp-down portion follows a natural curve dictated by the resilient structure of the valves and the slowing pump action but generally follows the reverse of the ramp-up geometry.

The relatively slow ramp up and down of the heart drive pump produces less wear and tear on the valve structures which leads to longer life. Such improved characteristics are useful for any pump in an inaccessible place such as implanted in the human body. But other uses for such a pump are clear as, for example, in space or in remote areas or down well shafts.

What is claimed is:

1. Artificial heart apparatus comprising a chamber for holding blood, said chamber including an inlet and an outlet having first and second check valves respectively, said apparatus also including pump drive means for alternatively reducing and increasing the volume of said chamber, said apparatus also including control means for controlling said drive means for providing a motor voltage which increases gradually, initially following a position of an imaginery curve to a constant drive value during a pump phase of operation of said apparatus such that shock to said check valves is reduced, said apparatus comprising biocompatable material.

2. Apparatus as set forth in claim 1 wherein said means for alternately increasing and reducing the volume of said chamber imposes alternate fill and empty cycles of operation on said chamber, and said means for controlling is operative to move said means for reducing the volume of said chamber during said empty cycle so that the pumped fluid pressure reaches a maximum value over a period of about one quarter of said empty cycle.

3. Apparatus as set forth in claim 2 wherein said means for reducing the volume of said chamber imposes a period of sixty cycles per minute and ramps up to the minimum chamber size over about one eighth second.

* * * * *